United States Patent [19]
Jona et al.

[11] Patent Number: 5,876,746
[45] Date of Patent: Mar. 2, 1999

[54] TRANSDERMAL PATCH AND METHOD FOR ADMINISTERING 17-DEACETYL NORGESTIMATE ALONE OR IN COMBINATION WITH AN ESTROGEN

[75] Inventors: Janan Jona, Sunnyvale; Jay Audett, Mountain View; Noel Singh, San Francisco, all of Calif.

[73] Assignee: Cygnus, Inc., Redwood City, Calif.

[21] Appl. No.: 660,024

[22] Filed: Jun. 6, 1996

Related U.S. Application Data

[63] Continuation-in-part of Ser. No. 517,263, Aug. 21, 1995, abandoned, which is a continuation-in-part of Ser. No. 473,531, Jun. 7, 1995, abandoned.

[51] Int. Cl.⁶ .......................... A61M 37/00; A61K 9/70; A61K 47/32; A61K 47/34
[52] U.S. Cl. ..................... 424/449; 424/448; 604/307
[58] Field of Search ..................................... 424/448, 449

[56] References Cited

U.S. PATENT DOCUMENTS

| | | |
|---|---|---|
| 4,668,232 | 5/1987 | Cordes et al. . |
| 4,898,920 | 2/1990 | Lee et al. . |
| 4,906,169 | 3/1990 | Chien et al. . |
| 4,994,267 | 2/1991 | Sablotsky . |
| 5,232,702 | 8/1993 | Pfister et al. . |
| 5,314,694 | 5/1994 | Gale et al. ............................ 424/448 |
| 5,376,377 | 12/1994 | Gale et al. . |
| 5,393,529 | 2/1995 | Hoffmann et al. . |
| 5,422,119 | 6/1995 | Casper ................................. 424/449 |
| 5,474,783 | 12/1995 | Miranda et al. . |
| 5,508,038 | 4/1996 | Wang et al. . |
| 5,656,286 | 8/1997 | Miranda et al. . |
| 5,665,377 | 9/1997 | Gonglla et al. . |
| 5,711,962 | 1/1998 | Cordes et al. . |

FOREIGN PATENT DOCUMENTS

| | | |
|---|---|---|
| 0 295 411 A1 | 12/1988 | European Pat. Off. . |
| 0 705 097 B1 | 3/1997 | European Pat. Off. . |
| 00655916 | 2/1998 | Germany . |
| 0 454 089 A1 | 10/1991 | Japan . |
| WO 98/03137 | 1/1998 | WIPO . |

OTHER PUBLICATIONS

Bringer, "Norgestimate: A clinical overview of a new progestin" *Am. J. Obstet. Gynecol.* (1992) 166:1969–1977.
McGuire et al., "Pharmacologic and pharmacokenetic characteristics of norgestimate and its metabolites" *Am. J. Obstet. Gynecol.* (1990) 163:2127–2131.

*Primary Examiner*—Edward J. Webman
*Attorney, Agent, or Firm*—Barbara G. McClung; Angela P. Horne; Roberta L. Robins

[57] ABSTRACT

Compositions and methods for preventing ovulation in a woman are provided, as well as compositions and methods for female hormone replacement therapy. The compositions can be administered by the use of a transdermal patch. The patch will administer 17-deacetyl norgestimate alone or in combination with an estrogen such as ethinyl estradiol to women via an adhesive matrix of a silicone and/or polyisobutylene.

41 Claims, No Drawings

TRANSDERMAL PATCH AND METHOD FOR ADMINISTERING 17-DEACETYL NORGESTIMATE ALONE OR IN COMBINATION WITH AN ESTROGEN

CROSS-REFERENCE TO RELATED APPLICATIONS

This application is a continuation-in-part of U.S. application Ser. No. 08/517,263, filed Aug. 21, 1995, now abandoned, which in turn is a continuation-in-part, of U.S. application Ser. No. 08/473,531, filed Jun. 7, 1995, now abandoned, the contents of which are hereby incorporated by reference.

DESCRIPTION +ps Technical Field

This invention relates to transdermal drug delivery. More particularly, it concerns patches and methods for transdermally administering 17-deacetyl norgestimate either alone or in combination with an estrogen, particularly ethinyl estradiol.

Background

Combinations of norgestimate (Ngm) and ethinyl estradiol (EE) are administered orally to women as a contraceptive. Bringer J., *Am. J. Obstet. Gynecol.* (1992) 166:1969–77. McGuire, J. C. et al., *Am. J. Obstet. Gynecol.* (1990) 163:2127–2131 suggests that orally administered Ngm metabolizes to 17-deacetyl norgestimate (17-d-Ngm), 3-ketonorgestimate, and levonorgestrel (Lng) and that these metabolites may contribute to the pharmacologic response to the orally administered drug.

Chien et al., U.S. Pat. No. 4,906,169 describes transdermal patches for co-delivering estrogens and progestins to women for contraception. EE is mentioned as one of the estrogens that may be administered from the patch and Ngm and Lng are mentioned as possible progestins that may be administered.

Applicants are unaware of any art describing the administration of 17-d-Ngm alone or in combination with any estrogen by transdermal or other routes of administration.

DISCLOSURE OF THE INVENTION

This invention provides compositions and a method for preventing ovulation or for providing hormone replacement therapy by the administration of an effective amount of 17-deacteyl norgestimate to a woman. In one aspect, the 17-deacteyl norgestimate is co-administered with an ovulation inhibiting amount of estrogen to the woman. The compositions are preferably administered transdermally.

Accordingly, one aspect of this invention is a transdermal patch for preventing ovulation in a woman comprising: a backing layer; and a matrix layer underlying the backing layer, the matrix layer comprising a mixture of 17-d-Ngm and a pressure sensitive adhesive and being adapted to be in diffusional communication with the skin of the woman and to administer an ovulation-inhibiting amount of 17-d-Ngm to said skin.

Another aspect of the invention is a transdermal patch for administering 17-d-Ngm and estrogen to a woman, the patch comprising: a backing layer; and a matrix layer underlying the backing layer, the matrix layer comprising a mixture of 17-d-Ngm, an estrogen, and a pressure sensitive adhesive, and being adapted to be in diffusional communication with the skin of the woman and to co-administer an ovulation-inhibiting amount of said 17-d-Ngm and estrogen to the woman through the skin. These patches are also can be used to provide hormone replacement therapy.

MODES FOR CARRYING OUT THE INVENTION

This invention provides compositions and methods for preventing ovulation in a woman comprising administering and an ovulation inhibiting amount of 17-deacteyl norgestimate. An effective amount can be from about 150 to about 350 $\mu$g/day and preferably from about 175 to about 300 $\mu$g/day of 17-deacteyl norgestimate. In one aspect, the 17-deacteyl norgestimate is co-administered with an ovulation inhibiting amount of an estrogen such as ethinyl estradiol. An effective amount is from about 150 to about 350 $\mu$g/day and preferably from about 175 to 300 $\mu$g/day of 17 deacteyl norgestimate and from 10 to 35 $\mu$g/day of ethinyl estradiol.

The transdermal patches of the invention provide contraception for women. They also are adapted for hormone replacement therapy.

The patches are intended to deliver 17-d-Ngm and, optionally an estrogen, to the skin continuously for an extended time period, typically 1–7 days and preferably for 7 days.

When the patches are worn for contraception, a patch will typically be placed on the skin on the fifth day of the menstrual cycle, and replaced as needed until 21 days of wearing have elapsed. For instance, in the case of a 7-day patch, three patches will be required to deliver the drug(s) for the 21-day period. If desired a placebo patch may be worn thereafter until the fifth day of the succeeding menstrual cycle. This regimen is repeated for each menstrual cycle.

17-d-Ngm and estrogens both inhibit ovulation, albeit by separate pathways. 17-d-Ngm inhibits the release of luteinizing hormone (LH), whereas the predominant effect of estrogen is to inhibit the secretion of follicle-stimulating hormone (FSH). Thus, when a combination of 17-d-Ngm and estrogen is administered according to the invention, ovulation is prevented by inhibiting the ovulatory stimulus and/or by inhibiting the growth of follicles. 17-d-Ngm administration is believed to be advantageous relative to the parent compound (Ngm) or its other metabolites in that 17-d-Ngm inhibits little or no androgenic activity.

The effective dose of 17-d-Ngm for inhibiting ovulation is normally in the range of about 150 to about 350 $\mu$g/day, preferably from about 175 to about 300 $\mu$g/day, and more preferably from about 175 to about 250 $\mu$g/day. The patches of the invention will typically have a basal surface area (i.e. the area in diffusional contact with the skin) between 10 and 50 cm$^2$. The effective dose of estrogen for inhibiting ovulation will depend upon the particular estrogen being co-administered. For instance, when the estrogen is ethinyl estradiol, the dose will normally be at least 10 $\mu$g/day, preferably from about 10 to 35 $\mu$g/day, and most preferably approximately 20 $\mu$g/day. The patches will contain sufficient amounts of 17-d-Ngm and, when present, estrogen, to provide such daily doses for the intended patch wear time. Typically, such doses are from about 20 $\mu$g/day to about 200 $\mu$g/day, and preferably from about 30 $\mu$g/day to 150 $\mu$g/day of ethinyl estradiol.

The patches of this invention are matrix or monolithic-type laminated structures. Such transdermal patches are well known in the art. They comprise a matrix layer of the drug(s) admixed with a pressure sensitive adhesive and a backing layer. The matrix serves as both the drug reservoir and the means by which the patch is affixed to the skin. Prior to use, the patch will also include an impermeable release liner layer.

The backing layer is impermeable to the drug and other components of the matrix and defines the top face surface of the patch. It may be made of a single layer or film of polymer, or be a laminate of one or more polymer layers and metal foil. Examples of polymers suitable for use in making backing films are polyvinylchloride, polyvinylidene chloride, polyolefins such as ethylene-vinyl acetate copolymers, polyethylene, and polypropylene, polyurethane, and polyesters such as polyethylene terephthalate.

The pressure-sensitive adhesive of the matrix will normally be a solution of polyacrylate, a silicone, or polyisobutylene (PIB). Such adhesives are well known in the transdermal art. See, for instance, the Handbook of Pressure Sensitive Adhesive Technology, 2nd Edition (1989) Van Nostrand, Reinhold.

Pressure sensitive solution polyacrylate adhesives are made by copolymerizing one or more acrylate monomers ("acrylate" is intended to include both acrylates and methacrylates), one or more modifying monomers, and one or more functional group-containing monomers in an organic solvent. The acrylate monomers used to make these polymers are normally alkyl acrylates of 4–17 carbon atoms, with 2-ethylhexyl acrylate, butyl acrylate, and isooctyl acrylate being preferred. Modifying monomers are typically included to alter the Tg of the polymer. Such monomers as vinyl acetate, ethyl acrylate and methacrylate, and methyl methacrylate are useful for this purpose. The functional group-containing monomer provides sites for crosslinking. The functional groups of these monomers are preferably carboxyl, hydroxy or combinations thereof Examples of monomers that provide such groups are acrylic acid, methacrylic acid and hydroxy-containing monomers such as hydroxyethyl acrylate. The polyacrylate adhesives are preferably crosslinked using a crosslinking agent to improve their physical properties, (e.g., creep and shear resistance). The crosslinking density should be low since high degrees of crosslinking may affect the adhesive properties of the copolymer adversely. Examples of crosslinking agents are disclosed in U.S. Pat. No. 5,393,529. Solution polyacrylate pressure sensitive adhesives are commercially available under tradenames such as GELVA™ and DURO-TAK™ from 3M.

Polyisobutylene adhesives are mixtures of high molecular weight (HMW) PIB and low molecular weight (LMW) PIB. Such mixtures are described in the art, e.g., PCT/US91/02516. The molecular weight of the HMW PIB will usually be in the range of about 700,000 to 2,000,000 Da, whereas that of the LMW PIB will typically range between 35,000 to 60,000. The molecular weights referred to herein are weight average molecular weight. The weight ratio of HMW PIB to LMW PIB in the adhesive will normally range between 1:1 to 1:10. The PIB adhesive will also normally include a tackifier such as polybutene oil and high Tg, low molecular weight aliphatic resins such as the ESCOREZ™ resins available from Exxon Chemical. Polyisobutylene polymers are available commercially under the tradename VISTANEX™ from Exxon Chemical.

The silicone adhesives that may be used in forming the matrix are typically high molecular weight polydimethyl siloxanes or polydimethyldiphenyl siloxanes. Formulations of silicone adhesives that are useful in transdermal patches are described in U.S. Pat. Nos. 5,232,702, 4,906,169 and 4,951,622.

Estrogens that may be combined with 17-d-Ngm in the matrix include 17-J-estradiol and esters thereof such as estradiol valerate, estradiol cypionate, estradiol acetate, estradiol benzoate, and EE. EE is a preferred estrogen for use in combination with 17-d-Ngm. EE/17-d-Ngm combinations may favorably effect metabolic parameters such as elevation of serum high density lipoprotein and reduction of the low density lipoprotein/high density lipoprotein ratio in serum.

In addition to the pressure sensitive adhesive, 17-d-Ngm, and optional estrogen, the matrix will typically contain sufficient amounts of permeation enhancers to increase the permeability of the 17-d-Ngm and estrogen through the skin and provide fluxes in the ranges described above. Examples of skin permeation enhancers that may be included in the matrix are described in U.S. Pat. Nos. 5,059,426, 4,973,468, 4,906,463 and 4,906,169, and include, but are not limited to lactate ester of $C_{12}$ to $C_{18}$ aliphatic alcohol, lauryl lactate, oleic acid or PGML. The amount of permeation enhancer included in the matrix will depend upon the particular enhancer(s) used. In most instances then enhancer will constitute in the range of 1 to 20% by weight of the matrix.

The matrix may contain other additives depending upon the particular adhesive used. For instance, materials, such as polyvinyl pyrrolidone (PVP), that inhibit drug crystallization, hygroscopic agents that improve the duration of wear, or additives that improve the physical (e.g., cold flow) or adhesive (e.g., tack, cohesive strength) properties of the matrix may be included.

The patches described above also are useful for providing hormone replacement therapy. When used to provide hormone replacement therapy, the matrix is constructed so as to provide an effective amount of 17-d-Ngm and estrogen for the intended purpose. Typically, the matrix and therefore the patch is constructed to provide from about 150 to about 350 μg/day, and preferably from about 175 to about 300 μg/day 17-d-Ngm co-administered with from about 5 to about 45 μg/day and preferably from about 10 to about 35 μg/day of an ethinyl estradiol. In an alternative embodiment, the patch will administer from about 200 to about 350 μg/day, and preferably from about 175 to about 300 μg/day 17-d-Ngm co-administered with from about 20 to about 175 μg/day and preferably from about 30 to about 150 μg/day of 17-β-estradiol. The patch is applied for 7 days and replaced with a new patch (for 7 days) for the duration of the therapy.

The patches of the invention may be fabricated using procedures known in the transdermal patch art. The procedure will generally involve formulating the matrix (i.e., mixing the adhesive, drug(s), permeation enhancer, and additives, if any), casting the matrix onto the backing or release liner layer, removing solvent from the matrix and applying the backing/release liner layer as the case may be. As is apparent to those of skill in the art, the matrix composition having an effective amount of the drug dispersed therein can be incorporated into various transdermal constructions and therefore, applicants are not limited to the embodiments exemplified below.

The following examples further illustrate the invention. These examples are not intended to limit the invention in any manner. Unless indicated otherwise, stated percentages are by weight.

EXAMPLES

Example 1

Duro-Tak 87-2287 is a solution polyacrylate adhesive available from National Starch and Chemical Co. Its monomer composition is: vinyl acetate, 2-ethylhexyl acrylate, hydroxyethyl acrylate, and glycidyl methacrylate. It contains no crosslinking agent. It is available as a 50% solids solution in ethyl acetate.

Mixtures of Duro-Tak 87-2287, 0.26% aluminum acetylacetonate crosslinker, 6% 17-d-Ngm, 1% EE, and various permeation enhancers were prepared. These mixtures were cured and cast as a 100 micron thick (wet) layer onto a 3M 1022 polyester backing and dried. Skin flux tests were carried out on the resulting assemblies according to the procedure described in col. 7 of U.S. Pat. No. 5,252,334. HPLC was used to assay for 17-d-Ngm and EE. A Perkin Elmer HPLC system with Diedoarray detector set at 245 nm and 215 nm for 17-d-Ngm and EE, respectively. The mobile phase was 55% water, 45% acetonitrile at a flow rate of 1.0 ml/min. Retention time was 4.5 and 3.0 min. for 17-d-Ngm and EE, respectively. Details of the formulations and the results of the flux tests are shown in Table 1 below.

TABLE 1

| Formulation | Flux ($\mu$g/cm$^2$/hr) | |
| --- | --- | --- |
|  | 17-d-Ngm | EE |
| 2% TG + 4% OL | 0.30 ± 0.04 | 0.061 ± 0.007 |
| 2% TG + 10% ML | 0.39 ± 0.03 | 0.076 ± 0.005 |
| 2% TG + 10% PGML | 0.29 ± 0.06 | 0.057 ± 0.009 |
| 3% TG | 0.24 ± 0.06 | 0.043 ± 0.011 |
| 4% TG + 15% ML | 0.38 ± 0.001 | 0.072 ± 0.002 |

TG = thioglycerol
OL = oleic acid
ML = methyl laurate
PGML = propylene glycol monolaurate Example 2

Silicone 4202 is a polydimethylsiloxane adhesive from Dow Corning. It was mixed with 17-d-Ngm, EE, 7% PVP (K30 from BASF; dissolved in n-propanol) and various enhancers. These mixtures were cast as a 100 micron thick (wet) layer onto a 3M 1022 polyester backing and dried. Skin flux tests were carried out on the resulting assemblies as in Example 1. The details of the formulations and the results of the flux studies are reported in Table 2 below.

TABLE 2

| % | | Formulation | Flux ($\mu$g/cm$^2$/hr) | |
| --- | --- | --- | --- | --- |
| 17-d-Ngm | % EE | Enhancer | 17-d-Ngm | EE |
| 4 | 0.5 | 5% ML + 1% TG | 0.65 ± 0.09 | 0.069 ± 0.007 |
| 6 | 0.5 | 5% ML + 1% TG | 0.60 ± 0.04 | 0.043 ± 0.004 |
| 6 | 0.5 | 14% PGML | 0.48 ± 0.04 | 0.070 ± 0.01 |
| 6 | 0.5 | 14% (TC:PGML; 80:20) | 0.58 ± 0.05 | 0.062 ± 0.01 |
| *4 | 0.5 | 4% TG + 5% ML | 0.64 ± 0.01 | 0.078 ± 0.01 |
| 4 | 0.5 | 2% ML | 0.51 ± 0.08 | 0.074 ± 0.008 |
| 2 | 0.5 | 2% TG + 2% ML | 0.71 ± 0.09 | 0.18 ± 0.02 |

TABLE 2-continued

| % | | Formulation | Flux ($\mu$g/cm$^2$/hr) | |
| --- | --- | --- | --- | --- |
| 17-d-Ngm | % EE | Enhancer | 17-d-Ngm | EE |

*Contains 14% PVP rather than 7% PVP.
TC = Transcutanol

Example 3

Comparison studies were done on silicone adhesive-17-d-Ngm/EE patches using two types of PVP: a soluble low molecular weight PVP designated PVP-K30 from BASF and an insoluble crosslinked micronized PVP designated PVP-CLM from BASF.

PVP-K30 is dissolved in absolute ethanol. Mixtures of 17-d-Ngm, EE and PVP-K30 were prepared and silicone 4202 and methyl laurate were added thereafter. The mixture was blended overnight. The mixture was cast on a 3M 1022 liner at a thickness of 15 mil (wet) and dried at 700 C. for 40 min.

PVP-CLM is available as micronized solids. Silicone 4202 and PVP-CLM were blended together and then methyl laurate, EE, 17-d-Ngm, and ethanol were added. The mixture was blended overnight and cast onto a 3M 1022 liner and dried as above.

Skin flux studies were carried out on the above-described assemblies as in Example 1. The details of these formulations and the results of the skin flux tests are reported in Table 3 below.

TABLE 3

| Formulation | Flux ($\mu$g/cm$^2$/hr) | |
| --- | --- | --- |
|  | 17-d-Ngm | EE |
| 0.1% EE, 1% 17-d-Ngm, 5% ML, 7% PVP-CLM, 86.9% silicone | 0.49 ± 0.02 | 0.05 ± 0.002 |
| 0.1% EE, 1% 17-d-Ngm, 5% ML, 7% PVP-K30, 86.9% silicone | 0.37 ± 0.07 | 0.04 ± 0.008 |

Example 4

PIB solutions were prepared by dissolving VISTANEX L100, Vistanex LM-MS-LC, and polybutene (Indopol H1900) in hexane. Suspensions of PVP-CLM, 17-d-Ngm, EE and various enhancers in ethanol/ethyl acetate were prepared. The PIB solution was added to the drug suspensions and the resulting mixtures were thoroughly blended. The mixtures were cast as a 10 mil thick (wet) layer onto release liners and dried at 70° C. for 40 min. Saranex 2015 backing was laminated to the subassembly. Skin flux studies were carried out on these assemblies as in Example 1. The details of these assemblies and the results of the skin flux studies are reported in Table 4 below.

TABLE 4

| PIB* | % EE | % 17-d-Ngm | % PVP-CLM | % Enhancer | Flux ($\mu$g/cm$^2$/hr) 17-d-Ngm | EE |
|---|---|---|---|---|---|---|
| 1:5:4 | 0.3 | 4.0 | 20 | 15, dibutylsebacate | 0.23 ± 0.02 | 0.06 ± 0.005 |
| 1:5:4 | 0.2 | 1.0 | 20 | 5,AMWAT | 0.32 ± 0.02 | 0.05 ± 0.004 |
| 1:5:4 | 0.2 | 4.0 | 20 | 5,lauric acid N,N-dimethyl amide | 0.33 ± 0.02 | 0.04 ± 0.001 |
| 2:4:4 | 0.3 | 4.0 | 20 | 20, propyl laurate | 0.35 ± 0.09 | 0.06 ± 0.002 |
| 1:5:4 | 0.2 | 2.0 | 20 | 5, lauramide diethanoiamine | 0.40 ± 0.05 | 0.06 ± 0.001 |
| 1:5:4 | 0.3 | 4.0 | 20 | 15, isopropyl palmitate | 0.44 ± 0.06 | 0.07 ± 0.001 |
| 1:5:4 | 0.3 | 4.0 | 20 | 15, ethyl oleate | 0.46 ± 0.06 | 0.10 ± 0.001 |
| 1:5:4 | 0.3 | 4.0 | 20 | 8, PGIS | 0.48 ± 0.04 | 0.10 ± 0.001 |
| 1:5:4 | 0.2 | 2.0 | 20 | 3, oleic acid | 0.60 ± 0.11 | 0.06 ± 0.002 |
| 1:5:4 | 0.2 | 3.0 | 20 | 3, oleic acid | 0.60 ± 0.24 | 0.04 ± 0.002 |
| 1:5:4 | 0.2 | 2.0 | 20 | 10, PGML | 0.59 ± 0.05 | 0.09 ± 0.001 |
| 1:5:4 | 0.2 | 3.0 | 20 | 10, PGML | 0.67 ± 0.07 | 0.07 ± 0.001 |
| 1:5:4 | 0.3 | 4.0 | 20 | 8/3, PGML/oleic acid | 0.79 ± 0.04 | 0.14 ± 0.001 |
| 1:5:4 | 0.2 | 2.0 | 20 | 10/0.5, PGML/oleic acid | 0.68 ± 0.09 | 0.10 ± 0.001 |

Example 5

A composition and matrix suitable for hormone replacement therapy is prepared as follows. 2% 17β-estradiol, 2% 17-deacetynorgetimate, 20% PVP-CLM and 76% PIB adhesive (1:5:2.5:1.5 Vistanex L100:Vistanex LM-MS-LC: Polybutene:Zonester 85FG) is dissolved in a combination of hexane, ethyl acetate, and ethanol. It was cast onto a polyester release liner and dried at 70° C. for 45 minutes. A polyester backing was applied prior to the flux study. The flux study was conducted as described as in Example 1.

TABLE 5

| Steroid | Flux ($\mu$g/cm$^2$/hr) |
|---|---|
| 71-d-Ngm | 0.10 |
| 71-β-estradiol | 0.20 |

Example 6

Transdermal patches having a matrix composed of PIB adhesive, PVP=CLM, lauryl or myristyl lactate, 17-d-Ngm, and EE were made as follows:

The 17-d-Ngm and EE were dissolved in ethyl acetate and the PVP-CL and lauryl lactate or myristyl lactate (obtained from ISP VanDYK of Belleville, N.J.) were added to that solution. A solution of the PIB adhesive (1:5:4 Vistanex L100:Vistanex LM-MS-LC:Indopol H1900) in hexane was added to the steroid solutions with vigorous mixing. N-propanol, at 10% of the PVP-CLM weight, was added slowly to the final mixtures. The mixtures were cast onto a release liner and dried in an oven at 70° C. for 40 minutes. The dried matrix weighed 7.5 mg/cm$^2$. The matrix-release liner subassembly was laminated to a polyester (Scotchpak 1012) backing. Another subassembly was laminated to a nonwoven polyester layer (Remay 2250). The release liner was removed from the backing assembly and it was applied to the nonwoven layer assembly to give a 5 layer composite of: backing/adhesive matrix/nonwoven/adhesive matrix/release liner.

Skin flux studies were carried out on these patches as described in Example 1. Details of the patches and the results of the flux studies are reported in Table 5 below.

TABLE 6

| Matrix Formulation | Skin Permeability | 17-d-Ngm Flux $\mu$g/cm$^2$/hr | EE flux $\mu$g/cm$^2$/hr |
|---|---|---|---|
| 72.85% PIB 20% PVP-CLM 0.15% EE 5% lauryl lactate | Low Medium High | 0.23 0.45 0.82 | 0.02 0.05 0.08 |
| 70.8% PIB 20% PVP-CLM 0.2% EE 2% 71-d-Ngm 7% lauryl lactate | Low Medium | 0.20 0.55 | 0.03 0.08 |
| 72.8% PIB 20% PVP-CLM 0.2 EE 2% 17-d-Ngm 5% myristyl lactate | — | 0.64 | 0.09 |

Modifications of the above-described modes for carrying out the invention that are obvious to those of skill in the field of transdermal patches are intended to be within the scope of the following claims.

We claim:

1. A transdermal patch for preventing ovulation in a woman comprising:
   a) a backing layer; and
   b) a non-acrylate containing matrix layer underlying the backing layer, the matrix layer comprising a mixture of 17-deacetyl norgestimate, lauryl lactate, and a pressure sensitive adhesive comprising at least one of a silicone and polyisobutylene, and being adapted to be in diffusional communication with the skin of the woman and to administer an ovulation-inhibiting amount of 17-deacetyl norgestimate.

2. The patch of claim 1 wherein said amount is 150 to 350 $\mu$g/day.

3. The patch of claim 1 wherein the pressure sensitive adhesive consists essentially of polyisobutylene and an aliphatic tackifier.

4. A transdermal patch for preventing ovulation in a woman comprising:
   a) a backing layer; and
   b) a non-acrylate containing matrix layer underlying the backing layer, the matrix layer comprising a mixture of 17-deacetyl norgestimate, an estrogen selected from the group consisting of ethinyl estradiol and 17-β-estradiol, lauryl lactate, and a pressure sensitive adhesive consisting essentially of polyisobutylene and an aliphatic tackifier, and being adapted to be in diffusional communication with the skin of a woman and to co-administer an ovulation inhibiting amount of 17-deacetyl norgestimate and estrogen to said woman.

5. The patch of claim 4 wherein the estradiol is ethinyl estradiol.

6. The patch of claim 5 wherein said amount is 150 to 350 µg/day of 17-deacteyl norgestimate and from 10 to 35 µg/day of ethinyl estradiol.

7. The patch of claim 4 where the estradiol is 17-β-estradiol.

8. The patch of claim 7 wherein said amount is 150 to 350 µg/day of 17-deacetyl norgestimate and from 30–150 µg/day of 17-β-estradiol.

9. A method of preventing ovulation in a woman comprising affixing to the skin of the woman the transdermal patch of claim 1.

10. The method of claim 9 wherein said amount is 150 to 350 µg/day.

11. A method of preventing ovulation in a woman comprising affixing to the skin of the woman the transdermal patch of claim 7.

12. The method of claim 11 wherein the estrogen is ethinyl estradiol.

13. The method of claim 12, wherein said amount is 150 to 350 µg/day of 17 deacteyl norgestimate and from 10 to 35 µg/day of ethinyl estradiol.

14. A transdermal patch for providing hormone replacement therapy in a woman comprising:
   a) a backing layer; and
   b) a non-acrylate containing matrix layer underlying the backing layer, the matrix layer comprising a mixture of 17-deacetyl norgestimate, an estrogen selected from the group consisting of ethinyl estradiol and 17-β-estradiol, lauryl lactate, and a pressure sensitive adhesive consisting essentially of polyisobutylene and an aliphatic tackifier, and being adapted to be in diffusional communication with the skin of a woman and to co-administer a therapeutic amount of 17-deacetyl norgestimate and estrogen to said skin.

15. The patch of claim 14 wherein the estradiol is ethinyl estradiol.

16. The patch of claim 14 wherein the estradiol is 17-β-estradiol.

17. A method of providing hormone replacement therapy in a woman comprising affixing to the skin of the woman the transdermal patch of claim 14.

18. The method of claim 17 wherein the estrogen is ethinyl estradiol.

19. The method of claim 17 wherein said amount of 17 deacetyl norgestimate is about 150 to 350 µg/day and the amount of ethinyl estradiol is from about 10 to 35 µg/day.

20. The patch of claim 3 wherein the tackifier comprises polybutene oil.

21. The patch of claim 3 wherein the matrix layer comprises crosslinked polyvinyl pyrrolidone.

22. The patch of claims 2 or 3 wherein the patch transdermally administers 150 to 350 µg/day of 17-deacetyl norgestimate for 7 consecutive days.

23. The patch of claim 4 wherein the tackifier comprises polybutene oil.

24. The patch of claim 4 wherein the matrix layer comprises crosslinked polyvinyl pyrrolidone.

25. The patch of claim 4 wherein the patch transdermally administers 150 to 350 µg/day of 17-deacetyl norgestimate and a therapeutically effective amount of estrogen for 7 consecutive days.

26. The method of claim 10 wherein the pressure sensitive adhesive consists essentially of polyisobutylene and an aliphatic tackifier.

27. The method of claims 10 or 26 wherein the matrix transdermally administers 150 to 350 µg/day of 17-deacetyl norgestimate for 7 consecutive days.

28. The method of claim 11 wherein the matrix transdermally administers 150 to 350 µg/day of 17-deacetyl norgestimate and a therapeutically effective amount of estrogen for 7 consecutive days.

29. The patch of claim 14 wherein the tackifier comprises polybutene oil.

30. The patch of claim 14 wherein the matrix layer comprises crosslinked polyvinyl pyrrolidone.

31. A transdermal patch comprising:
   a backing layer; and
   a non-acrylate containing matrix layer underlying the backing layer, the matrix layer comprising a mixture of 17-deacetyl norgestimate, crosslinked polyvinyl pyrrolidone, and a pressure sensitive adhesive consisting essentially of polyisobutylene and an aliphatic resin tackifier, wherein the matrix is adapted to be in diffusional communication with skin to transdermally administer a therapeutically effective amount of 17-deacetyl norgestimate for 7 consecutive days.

32. The patch of claim 31 wherein the therapeutically effective amount of 17-deacetyl norgestimate prevents ovulation.

33. The patch of claim 31 wherein the matrix administers from 150 to 350 µg/day of 17-deacetyl norgestimate.

34. The patch of claim 31 wherein the tackifier comprises polybutene oil.

35. The patch of claim 31 wherein the matrix further comprises a skin permeation enhancer.

36. The patch of claim 35 wherein the skin permeation enhancer comprises lauryl lactate.

37. The patch of claim 31 wherein the matrix further comprises an estrogen.

38. The patch of claim 37 wherein the estrogen comprises ethinyl estradiol.

39. A method for transdermally administering 17-deacetyl norgestimate by applying the transdermal patch of claim 31 to the skin of a patient such that the matrix is in diffusional communication with the skin.

40. The method of claim 39 wherein the transdermal administration of 17-deacetyl norgestimate is effective to prevent ovulation.

41. The method of claim 39 wherein the transdermal administration of 17-deacetyl norgestimate is effective to provide hormone therapy.

* * * * *

UNITED STATES PATENT AND TRADEMARK OFFICE

(12)      CERTIFICATE EXTENDING PATENT TERM
UNDER 35 U.S.C. § 156

| | | | |
|---|---|---|---|
| (68) | PATENT NO. | : | 5,876,746 |
| (45) | ISSUED | : | March 2, 1999 |
| (75) | INVENTOR | : | Janan Jona et al. |
| (73) | PATENT OWNER | : | Ortho-McNeil Pharmaceutical, Inc. |
| (95) | PRODUCT | : | ORTHO-EVRA® (norelgestromin and ethinyl estradiol) |

This is to certify that an application under 35 U.S.C. § 156 has been filed in the United States Patent and Trademark Office, requesting extension of the term of U.S. Patent No. 5,876,746 based upon the regulatory review of the product ORTHO-EVRA® (norelgestromin and ethinyl estradiol) by the Food and Drug Administration. Since it appears that the requirements of the law have been met, this certificate extends the term of the patent for the period of

(94)                 166 days from June 7, 2015, the original expiration date of the patent, subject to the payment of maintenance fees as provided by law, with all rights pertaining thereto as provided by 35 U.S.C. § 156(b).

I have caused the seal of the United States Patent and Trademark Office to be affixed this 9th day of February 2006.

Jon W. Dudas
Under Secretary of Commerce for Intellectual Property and Director of the United States Patent and Trademark Office

UNITED STATES PATENT AND TRADEMARK OFFICE
CERTIFICATE OF CORRECTION

PATENT NO. : 5,876,746
DATED : March 2, 1999
INVENTOR(S) : Janan JONA, Jay AUDETT and Noel SINGH It is certified that error appears in the above-identified patent and that said Letters Patent is hereby corrected as shown below:

Claim 11, line 3: "patch of claim 7" should be --patch of claim 4--.

Signed and Sealed this

Sixth Day of July, 1999

Attest:

Q. TODD DICKINSON

Attesting Officer

Acting Commissioner of Patents and Trademarks